(12) United States Patent
Taha et al.

(10) Patent No.: US 6,564,090 B2
(45) Date of Patent: May 13, 2003

(54) METHOD AND APPARATUS FOR THE SERIAL COMPARISON OF ELECTROCARDIOGRAMS

(75) Inventors: Basel H. Taha, Menomonee Falls, WI (US); Shankara B. Reddy, Cedarburg, WI (US); Joel Q. Xue, Germantown, WI (US)

(73) Assignee: GE Medical Systems Information Technologies, Inc., Milwaukee, WI (US)

(*) Notice: Subject to any disclaimer, the term of this patent is extended or adjusted under 35 U.S.C. 154(b) by 0 days.

(21) Appl. No.: 09/682,733

(22) Filed: Oct. 11, 2001

(65) Prior Publication Data

US 2003/0073914 A1 Apr. 17, 2003

(51) Int. Cl.[7] .............................................. A61B 5/0402
(52) U.S. Cl. ..................................................... 600/509
(58) Field of Search .......................... 600/509, 515–518

(56) References Cited

U.S. PATENT DOCUMENTS

| | | | |
|---|---|---|---|
| 5,253,650 A | 10/1993 | Wada | 600/525 |
| 5,410,473 A | 4/1995 | Kaneko et al. | 600/523 |
| 5,690,118 A * | 11/1997 | Sornmo et al. | 600/508 |
| 6,171,256 B1 | 1/2001 | Joo et al. | 600/508 |
| 6,230,048 B1 * | 5/2001 | Selvester et al. | 600/523 |

OTHER PUBLICATIONS

Rowlandson, Ian G., US2002/0087355–A1, "Automated Scheduling of Emergency Procedure Based On Identification of High–Risk Patient", Jul. 4, 2002.*

Rowlandson, Ian G., US 2002/0042579–A1, "Method and Apparatus for Perioperative Assessment of Cardiovascular Risk", Apr. 11, 2002.*

Braunwald, E., Antman, E.M., Beasley, J.W., Califf, R.M., Cheitlin, M.D., Hochman, J.S., Jones, R.H., Kereiakes, D., Kupersmith, J., Levin T.N., Pepine, C.J., Schaeffer, J.W., Smith E.E. III, Steward D.E. Theroux; ACC/AHA 2002 Guideline Update for the Management of Patients with Unstable Angina and non–ST–segment Elevation Myocardial Infraction: a report of the American College of Cardiology/American Heart Association Task Force on Practice Guidelines.

Bertrand, M.E., "Management of Acute Coronary Syndromes: Acute Coronary Syndromes Without Persistent ST Segment Elevation," European Heart Journal; Sep. 2000; pp. 1406–1432; vol. 21, issue 17; The European Society of Cardiology.

(List continued on next page.)

Primary Examiner—Carl Layno
(74) Attorney, Agent, or Firm—Michael Best & Friedrich LLP (57) ABSTRACT

A method and apparatus for performing serial comparison between electrocardiograms (ECGs) acquired from a patient. The method includes acquiring ECGs from a patient with an acquisition device and using the acquisition device to perform a serial comparison between at least two of the acquired ECGs. The apparatus is an acquisition device including an acquisition module for acquiring ECGs from a patient and a signal processor for performing a serial comparison between at least two of the acquired ECGs.

50 Claims, 6 Drawing Sheets

OTHER PUBLICATIONS

Ryan, T.J., Antman, E.M., Brooks, N.H., Califf, R.M., Hillis, L.D., Hiratzka, L.F., Rapaport, E., Riegel, B., Russell, R.O., Smith, E.E. III, Weaver, W.D.; ACC/AHA Guidelines for the Management of Patients with Acute Myocardial Infarction: 1999 Update: a report of the American College of Cardiology/American Heart Associate Task force on Practice Guidelines (Committee on Management of Acute Myocardial Infarction).

O'Rouke, M.F., Cook, A., Carroll, G., Gallagher, D., Hall, J.; "Accuracy of a Portable Interpretive ECG Machine in Diagnosis of Acute Evolving Myocardial Infarction;" Australian New Zealand Journal of Medicine; Feb. 1992; pp. 9–13; vol. 22(1).

Kudenchuk, P.J., Ho, M.T., Weaver, W.D., Litwin, P.E., Martin, J.S., Eisenberg, M.S., Hallstrom, A.P., Cobb, L.A., Kennedy, J.W.; "Accuracy of Computer–Interpreted Electrocardiography in Selecting Patients for Thrombolytic Therapy;" Journal of American College of Cardiology; Jun. 1991; pp. 148691; vol. 17(7).

* cited by examiner

METHOD AND APPARATUS FOR THE SERIAL COMPARISON OF ELECTROCARDIOGRAMS

BACKGROUND OF INVENTION

The invention relates generally to a method and apparatus for the serial comparison of electrocardiograms (ECGs), and more specifically to a method and apparatus for the serial comparison of ECGs using an ECG acquisition device.

When a patient is suffering from severe chest pain, clinicians must detect acute coronary syndromes, such as acute myocardial infarction and acute cardiac ischemia, quickly and accurately in order to prevent the death of cardiac muscle and, ultimately, the death of the patient. The ECG is critical for evaluating severe chest pain in a patient in order to detect and manage acute coronary syndromes.

When a patient suffering from severe chest pain is admitted into an emergency room, a single, initial ECG is immediately taken and analyzed by an emergency room clinician or by a computerized ECG interpretation program. Similarly, when emergency medical technicians arrive to care for a patient suffering from severe chest pain, a single, initial ECG is immediately taken and analyzed by the emergency medical technicians. Based on the analysis of these single, initial ECGs, acute myocardial infarction is only accurately detected one-half of the time and acute cardiac ischemia is only accurately detected one-third of the time. These poor detection rates are due to the fact that almost two-thirds of all ischemic episodes that occur in patient's suffering from unstable coronary artery disease are silent and cannot be detected by the analysis of a single ECG. Also, fifteen to thirty percent of patients with unstable coronary disease have transient episodes of ST segment changes, predominately ST segment depression, that cannot be detected by the analysis of a single ECG. Similarly, acute coronary syndrome cannot be diagnosed based on a left bundle branch block appearing in a single ECG, because left bundle branch block is only associated with acute coronary syndrome if it is new, i.e., if the left bundle branch block has not occurred in the patient's previous ECGs and then suddenly occurs in a subsequent ECG. However, it is desirable to detect new left bundle branch block, because new left bundle branch block is one of the strongest predictors of mortality in acute coronary syndrome patients.

The serial comparison of multiple ECGs can reveal acute coronary syndromes more accurately than the analysis of a single ECG. For example, if a clinician performs a serial comparison between an ECG acquired while the patient is in a stable cardiac period and a subsequent ECG indicating a left bundle branch block, the clinician can determine whether the left bundle branch block is new in order to predict acute myocardial infarction. If the serial comparison is performed by the clinician while the patient is suffering from severe chest pain, the clinician can detect and treat the myocardial infarction appropriately in a timely basis. Similarly, if a clinician performs a serial comparison while the patient is suffering from severe chest pain, the clinician can more accurately detect changes in the ST segment and changes in the amplitude of the T wave in order to predict acute cardiac ischemia and evolving acute myocardial infarction.

Even though the serial comparison of multiple ECGs can reveal acute coronary syndromes more accurately than the analysis of a single ECG, the existing ECG analysis programs used to perform serial comparisons have several limitations. ECG analysis programs for performing serial comparisons are generally implemented in ECG management systems, such as the GE Medical Systems Information Technologies, Inc. MUSE system, or in specially-designed ST segment monitoring devices, such as the GE Medical Systems Information Technologies, Inc. ST-Guard device. However, few emergency departments have access to ECG management systems or are equipped with specially-designed ST segment monitoring devices in order to perform serial comparisons quickly and accurately enough to detect acute coronary syndromes in patients suffering from severe chest pain. In the case of emergency medical technicians caring for a patient suffering from severe chest pain away from the hospital, a serial comparison cannot be performed between the patient's ECGs stored in the ECG management system at the hospital and the ECGs acquired from the patient by the emergency medical technicians in time for the emergency medical technicians to detect and manage the patient's acute coronary syndrome. Moreover, the serial comparison algorithms implemented in the ECG management systems are not designed specifically for detecting acute coronary syndromes, and thus, lack the sensitivity required to detect acute coronary syndromes in the most accurate manner.

SUMMARY OF INVENTION

In light of the limitations described above, a need exists for a method and apparatus for performing a serial comparison between a patient's ECGs quickly and accurately in order to detect acute coronary syndrome in a patient suffering from severe chest pain, such as when a patient is admitted to an emergency room or when an emergency medical technician is treating a patient away from the hospital. Moreover, a need exists for a method and apparatus for ruling out acute coronary syndrome in order to discharge patients more quickly from the emergency room.

Accordingly, the invention provides a method and apparatus for acquiring ECGs from a patient with an ECG acquisition device and using the ECG acquisition device to perform a serial comparison between two or more of the ECGs acquired from the patient in order to accurately detect acute coronary syndromes.

The apparatus is an acquisition device for acquiring ECGs from a patient. The acquisition device includes an acquisition module for acquiring ECGs from the patient and a signal processor coupled to the acquisition module for performing a serial comparison between two or more of the ECGs acquired from the patient. The acquisition device may perform the serial comparison in real-time as ECGs are acquired from the patient in order to detect acute coronary syndrome. The acquisition device may be used to perform the serial comparison between the first ECG acquired from the patient during the cardiac episode, i.e., an index ECG, and subsequent ECGs. In addition, the acquisition device may be physically or wirelessly coupled to an ECG management system in order to access an ECG acquired from the patient during a stable cardiac period, i.e., a baseline ECG. If the acquisition device is wirelessly coupled to the ECG management system, the acquisition device may include a receiver for wirelessly communicating with an ECG management system located in a hospital remote from the acquisition device in order to access the patient's baseline ECG stored in the ECG management system. The acquisition device is used to perform serial comparisons between the baseline ECG, the index ECG, and the subsequent ECGs.

For the method of the invention, ECGs are acquired from a patient with an ECG acquisition device and the ECG acquisition device is used to perform a serial comparison between two or more of the acquired ECGs. The serial comparison may be performed in real-time as ECGs are acquired from the patient in order to detect acute coronary syndrome. The serial comparison is performed between an index ECG and subsequent ECGs. The method may also include accessing a baseline ECG from an ECG management system coupled to the acquisition device or an ECG management system located in a hospital remote from the acquisition device. The serial comparisons may be performed between the baseline ECG, the index ECG, and the subsequent ECGs.

The invention also provides a method of performing a serial comparison between ECGs in order to accurately detect acute coronary syndrome. The method includes acquiring an index ECG and subsequent ECGs and identifying changes between the index ECG and the subsequent ECGs in QRS complex, ST elevation, ST depression, or T wave. The method also includes assigning severity values to the identified changes and analyzing the severity values according to a fuzzy logic algorithm. Acute myocardial infarction is indicated to a clinician if the severity value of the changes in the QRS complex is high, if the severity value of the changes in the ST elevation is high, if the severity value of the changes in the ST elevation and the ST depression are moderate, or if the severity value of the changes in the T wave inversion is equal to or greater than moderate. Acute ischemia is indicated to a clinician if the severity value of the changes in the ST depression is high, or if the severity level of the changes in the ST depression and the T wave inversion are moderate.

The invention further provides a software program for implementation in an ECG acquisition device and for performing a serial comparison between two or more ECGs acquired from a patient. The software program includes a management module for analyzing corresponding leads of the ECGs, for determining which corresponding leads indicate differences between the ECGs, for sorting the corresponding leads into groups according to the indicated differences, and for assigning a severity value to each one of the groups. The software program also includes a decision logic module for implementing a fuzzy logic algorithm to analyze the severity value assigned to each one of the groups and for outputting an indication of an acute coronary syndrome based on the analysis.

Various other features and advantages of the invention are set forth in the following drawings, detailed description and claims.

DETAILED DESCRIPTION

Before one embodiment of the invention is explained in full detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of including and comprising and variations thereof herein is meant to encompass the items listed thereafter and equivalents thereof as well as additional items.

Figure 1:
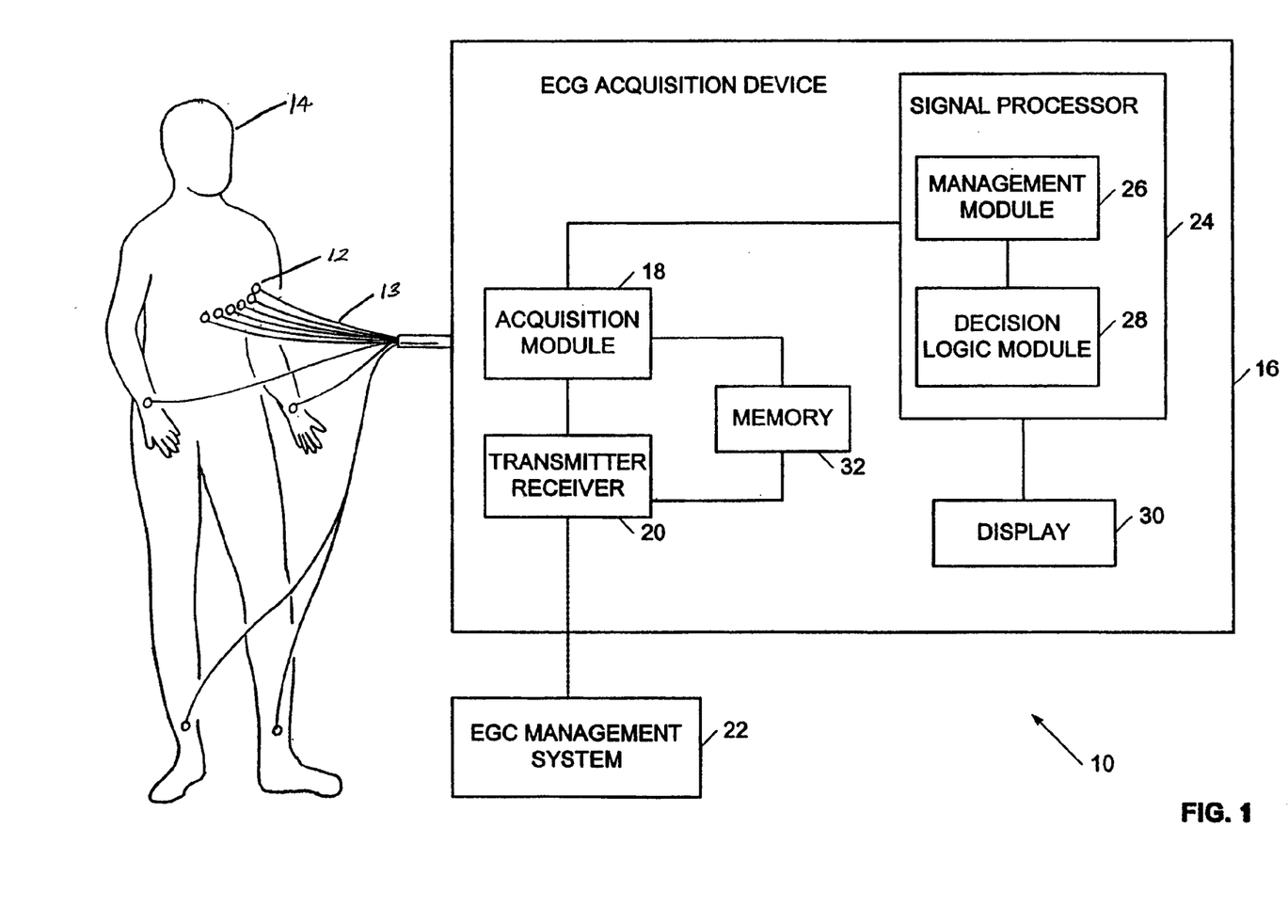
FIG. 1 illustrates the apparatus embodying the invention connected to a patient.

FIG. 1 illustrates an ECG device 10 embodying the invention. The ECG device 10 includes electrodes 12 attached to a patient 14. Ten electrodes 12 may be attached to the patient 14 in order to acquire a standard, twelve-lead ECG. However, any number of electrodes 12 may be attached to the patient 14 in any manner suitable for acquiring one or more leads of ECG data. The electrodes 12 are coupled via leadwires 13 to an ECG acquisition device 16. The ECG acquisition device 16 may be any device capable of acquiring ECGs, such as a cardiograph, a Holter monitor, an event recorder, or a stress ECG machine.

The ECG acquisition device 16 includes an acquisition module 18 for coordinating the acquisition of ECGs from the patient 14. The acquisition module 18 acquires a first ECG from the patient 14 and designates the first ECG as the index ECG for the patient 14. The acquisition module 18 also acquires subsequent ECGs from the patient 14 for any time period desired by a clinician, such as for the extent of a cardiac episode.

The ECG acquisition device 16 may be physically or wirelessly coupled to an ECG management system 22. The ECG acquisition device 16 preferably includes a transmitter/receiver device 20 coupled to the acquisition module 18 for wirelessly communicating with an ECG management system 22 at a hospital in a location remote from the ECG acquisition device 16. The acquisition module 18 wirelessly communicates with the ECG management system 22 via the transmitter/receiver device 20 in order to acquire a baseline ECG, i.e., an ECG acquired from the patient 14 during a stable cardiac period, from the ECG management system 22. The transmitter/receiver device 20 is coupled to memory 32 in order to store the baseline ECG after the baseline ECG is acquired so that the baseline ECG can be used for later serial comparisons. The index ECG and the subsequent ECGs acquired with the ECG acquisition device 16 may also be stored in the memory 32. The acquisition module 18 also wirelessly communicates with the ECG management system 22 via the transmitter/receiver device 20 in order to transmit the index ECG and the subsequent ECGs stored in the memory 32 to the ECG management system 22 for further analysis or for long-term storage.

The acquisition module 18 is coupled to a signal processor 24. The signal processor 24 performs serial comparisons between the baseline ECG, the index ECG, and the subsequent ECGs. The signal processor 24 includes a management module 26 which receives the baseline ECG, the index ECG, and the subsequent ECGs from the acquisition module 18. The management module 26 also coordinates and performs serial comparisons between several sets of ECGs at once. The management module 26 performs serial comparisons between any two ECGs, such as between the baseline ECG and the index ECG, between the baseline ECG and one of the subsequent ECGs, between the index ECG and one of the subsequent ECGs, or between two of the subsequent ECGs. The management module 26 preferably performs the serial comparisons in real-time as subsequent ECGs are acquired from the patient 14.

The management module 26 is coupled to a decision logic module 28. The decision logic module 28 is used to implement a fuzzy logic algorithm that analyzes the results of the serial comparisons performed by the management module 26. The decision logic module 28 uses the fuzzy: logic algorithm to analyze the results of the serial comparisons and then sends the results of the analysis to a display 30 coupled to the signal processor 24 in order to indicate to a clinician whether the patient 14 is suffering from an acute coronary syndrome.

Figure 2A:
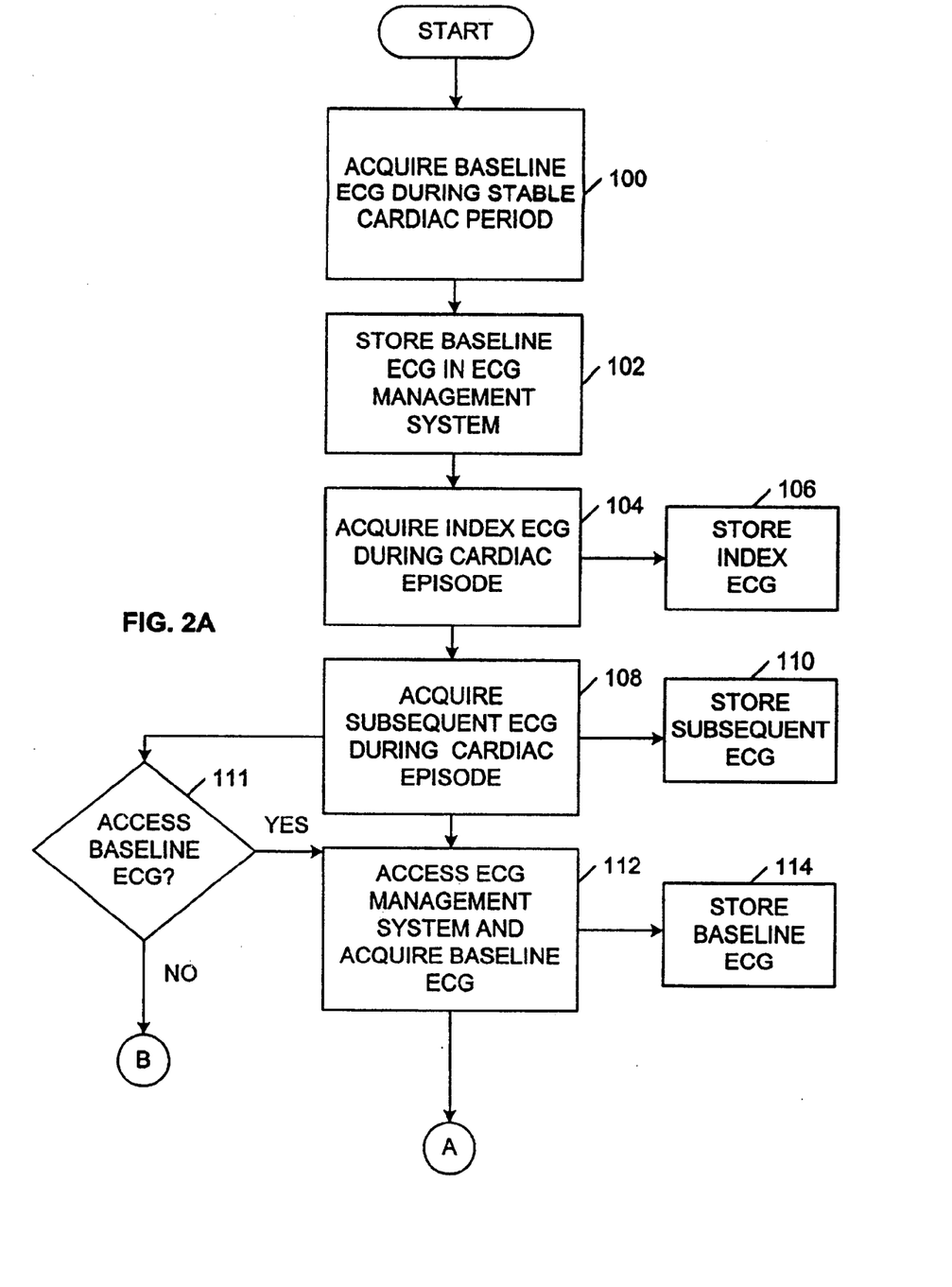
FIGS. 2A, 2B, 2C, and 2D are flow charts illustrating the method of the invention.

FIGS. 2A, 2B, 2C, and 2D illustrate the method of the invention. Referring to FIGS. 1 and 2A, a baseline ECG is acquired (at 100) from the patient 14 during a stable cardiac period. The baseline ECG may be acquired (at 100) several days or even several years prior to the patient 14 being treated for severe chest pain during a cardiac episode. The baseline ECG is generally acquired (at 100) during a standard, twelve-lead ECG test, such as an ECG stress test, when the patient 14 is in a clinic or hospital. The baseline ECG is stored (at 102) in the ECG management system 22.

When the patient 14 is being treated for severe chest pain during a cardiac episode, such as in an emergency room at a hospital or at a location remote from a hospital, the electrodes 12 and leadwires 13 are attached to the patient 14 and an initial ECG, i.e., the index ECG, is acquired (at 104). Thus, the index ECG is the first ECG acquired (at 104) from the patient 14 during the cardiac episode. The index ECG is stored (at 106) in the memory 32 of the ECG acquisition device 16 and designated as such, so that the index ECG can be differentiated from subsequent ECGs acquired from the patient 14. Subsequent ECGs are then acquired (at 108) from the patient 14 for any period of time desired by the clinician, such as for the extent of a cardiac episode. The subsequent ECGs are stored (at 110) in the memory 32 of the ECG acquisition device 16. Once the index ECG is acquired (at 104) and one or more subsequent ECGs are acquired (at 108), serial comparisons may be performed between the index ECG and the subsequent ECGs. The time period between each serial comparison may be from twenty seconds to several hours.

However, rather than only performing serial comparisons between the index ECG and the subsequent ECGs, a baseline ECG for the patient 14 is preferably acquired from the ECG management system 22. The ECG acquisition device 16 is used to determine (at 111) whether a baseline ECG should be acquired. In one preferred embodiment, the management module 26 outputs to the display 30 a request for the clinician to decide whether the baseline ECG should be acquired. For example, the clinician may press a button on a housing of the ECG acquisition device 16 or the clinician may press a touchscreen button on the display 30 of the ECG acquisition device 16 in order to indicate whether the baseline ECG for the patient 14 should be acquired.

In another preferred embodiment, the acquisition module 18 automatically attempts to communicate with the ECG management system 22 in order to acquire the baseline ECG for the patient 14. For example, the acquisition module 18 first automatically attempts to access the ECG management system 22 via a physical connection. If the ECG acquisition device 16 is not physically connected to the ECG management system 22, the acquisition module 18 automatically attempts to access the ECG management system 22 via the transmitter/receiver 20.

Once the acquisition module 18 establishes communication with the ECG management system 22 and acquires (at 112) the baseline ECG, the baseline ECG is stored (at 114) in the memory 32 of the ECG acquisition device 16, so that the baseline ECG can be used for later serial comparisons. Once the baseline ECG is acquired (at 112), the management module 26 can perform serial comparisons between the baseline ECG, the index ECG, and the subsequent ECGs.

Figure 2B:
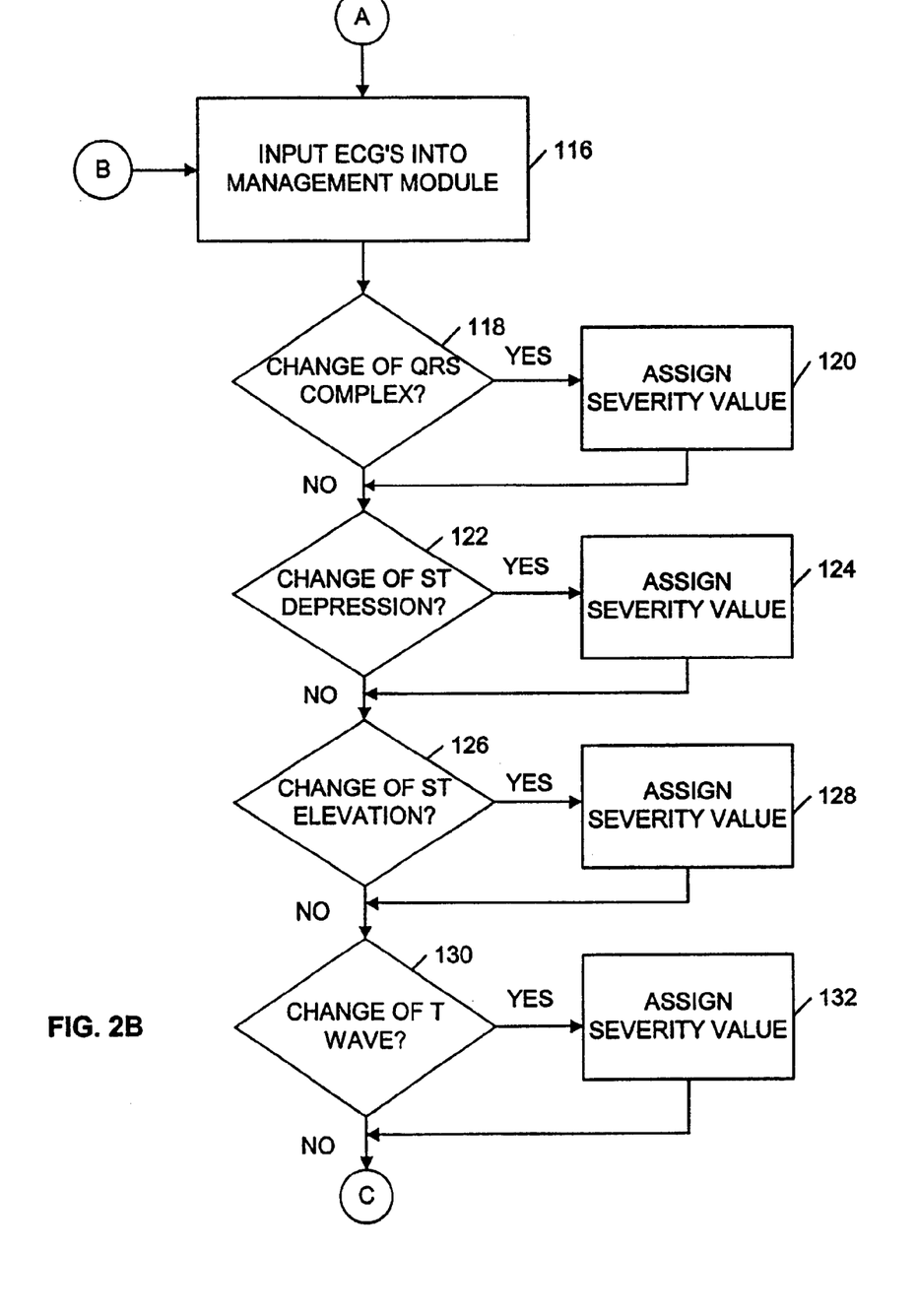

Referring to FIGS. 1 and 2B, the acquired ECGs from the acquisition module 18 are input into (at 116) the management module 26 of the signal processor 24. The management module 26 coordinates multiple serial comparisons between several sets of ECGs at once. The management module 26 first determines which leads of the pair of ECGs correspond to one another. For example, for a serial comparison between the baseline ECG and the index ECG for the patient 14, the management module 26 determines which leads of the baseline ECG correspond to the leads of the index ECG, e.g., lead V1 of the baseline ECG corresponds to lead V1 of the index ECG and lead V2 of the baseline ECG corresponds to lead V2 of the index ECG. Typically, for standard, twelve-lead ECGs, the management module 26 will determine that twelve leads of the baseline ECG correspond to twelve leads of the index ECG. However, the ECG acquisition device 16 may not acquire all twelve leads for a standard, twelve-lead ECG, while the baseline ECG is preferably a standard, twelve-lead ECG. In this case, the management module 26 will determine which leads are acquired by the ECG acquisition device 16 and determine which leads of the baseline ECG correspond to the leads acquired by the acquisition device 16.

Once the management module 26 has determined which leads correspond to one another, the management module 26 analyzes the sets of corresponding leads according to several functional blocks. The functional blocks represent various portions of a typical ECG waveform, as illustrated in FIG. 3. In one preferred embodiment, the functional blocks represent the P wave, the Q wave, the QRS complex, the ST elevation, the ST depression, the T wave, and the QT interval. In general, the management module 26 determines which sets of corresponding leads exhibit changes in a portion of the ECG waveform represented by one of the functional blocks. If a set of corresponding leads exhibits changes in a portion of the ECG waveform represented by one of the functional blocks, the set of corresponding leads is divided into a group associated with that functional block. Once all of the sets of corresponding leads are analyzed and divided into groups associated with the functional blocks, each of the groups associated with the functional blocks are assigned a severity value. A preferred embodiment of the analysis performed by the management module 26 is described below with respect to FIGS. 2B and 2C.

Referring to FIGS. 1 and 2B, the management module 26 first analyzes each of the corresponding leads to determine (at 118) if there is a change in the QRS complex in order to detect a new bundle branch block, i.e., either left bundle branch block or right bundle branch block. The management module 26 determines if there are changes in the duration and the amplitude of the QRS complex. The sets of corresponding leads indicating a change in the QRS complex are divided into the QRS functional block. Once all the sets of corresponding leads are analyzed and divided, the management module 26 assigns (at 120) a severity value to the QRS functional block. Preferably, a high severity value (e.g., a severity value of 2) is assigned to the QRS functional block if all of the following are true: (1) if the QRS complex duration for the second ECG of any of the corresponding leads is greater than 120 milliseconds, while the QRS complex duration for the first ECG of any of the corresponding leads is less than 120 milliseconds; (2) if the QRS complex in any of the corresponding V1 and V2 leads is negative and either one of the Q wave or the S wave has a duration greater than 80 milliseconds; or (3) in any two of the corresponding I, V5, and V6 leads, if the sum of the durations of the R wave (i.e., the first positive deflection in the QRS complex) and the R" wave (i.e., a second positive deflection that sometimes occurs in the QRS complex) is greater than 100 milliseconds.

The management module 26 then analyzes each of the sets of corresponding leads to determine (at 122) if there is a change in ST depression in order to detect acute ischemia and acute myocardial infarction. The management module 26 determines if there are amplitude changes that indicate ST depression between the sets of corresponding leads at the following points in the ECG waveform: STJ (the beginning of the ST segment), STM (the beginning of the ST segment plus the average interval between R wave peaks divided by 16), STE (the beginning of the ST segment plus the average interval between R wave peaks divided by 8), STJ+40 (the beginning of the ST segment plus 40 milliseconds), STJ+80 (the beginning of the ST segment plus 80 milliseconds), and ST slope (whether up, down, or flat). The corresponding leads indicating ST depression are divided into the ST depression functional block. Once all the sets of corresponding leads are analyzed and divided, the management module 26 assigns (at 124) a severity value to the ST depression functional block. Preferably, if the ST depression change between any of the corresponding leads is greater than negative 100 microvolts, a high severity value is assigned to the ST depression functional block. If the ST depression change between any of any of the corresponding leads is between negative 70 microvolts and negative 100 microvolts, a moderate severity value (e.g., a severity value of 1) is assigned to the ST depression functional block.

The management module 26 then analyzes each of the corresponding leads to determine (at 126) if there is a change in ST elevation in order to detect acute myocardial infarction. The management module 26 determines if there are amplitude changes that indicate ST elevation between the sets of corresponding leads at the following points in the ECG waveform: STJ (the beginning of the ST segment), STM (the beginning of the ST segment plus the average interval between R wave peaks divided by 16), STE (the beginning of the ST segment plus the average interval between R wave peaks divided by 8), STJ+40 (the beginning of the ST segment plus 40 milliseconds), STJ+80 (the beginning of the ST segment plus 80 milliseconds), and ST slope (whether up, down, or flat). The sets of corresponding leads indicating ST elevation are divided into the ST elevation functional block. Once all the sets of corresponding leads are analyzed and divided, the management module 26 assigns (at 128) a severity value to the change of ST elevation functional block. Preferably, if the ST elevation between any of the corresponding precordial leads (i.e., leads V1, V2, V3, V4, V5, and V6) is greater than 200 microvolts, or if the ST elevation between any of the corresponding limb leads (i.e., leads I, II, III, AVR, AVL, and AVF) is greater than 100 microvolts, a high severity value is assigned to the ST elevation block. If the ST elevation between any of the corresponding precordial leads is between 100 microvolts and 200 microvolts, or if the ST elevation between any of the corresponding limb leads is between 70 microvolts and 100 microvolts, a moderate severity value is assigned to the ST elevation block.

The management module 26 then analyzes each of the sets of corresponding leads to determine (at 130) if there is a change in the T wave in order to detect acute ischemia and acute myocardial infarction. The management module 26 determines if there are changes in the amplitude and morphology of the T wave. The sets of corresponding leads indicating a change in the T wave are divided into the T wave functional block. Once all the sets of corresponding leads are analyzed and divided, the management module 26 assigns (at 132) a severity value to the T wave functional block. Preferably, if the inversion of the T wave is greater than 200 microvolts between any of the corresponding leads, a high severity value is assigned to the T wave functional block.

Figure 2C:
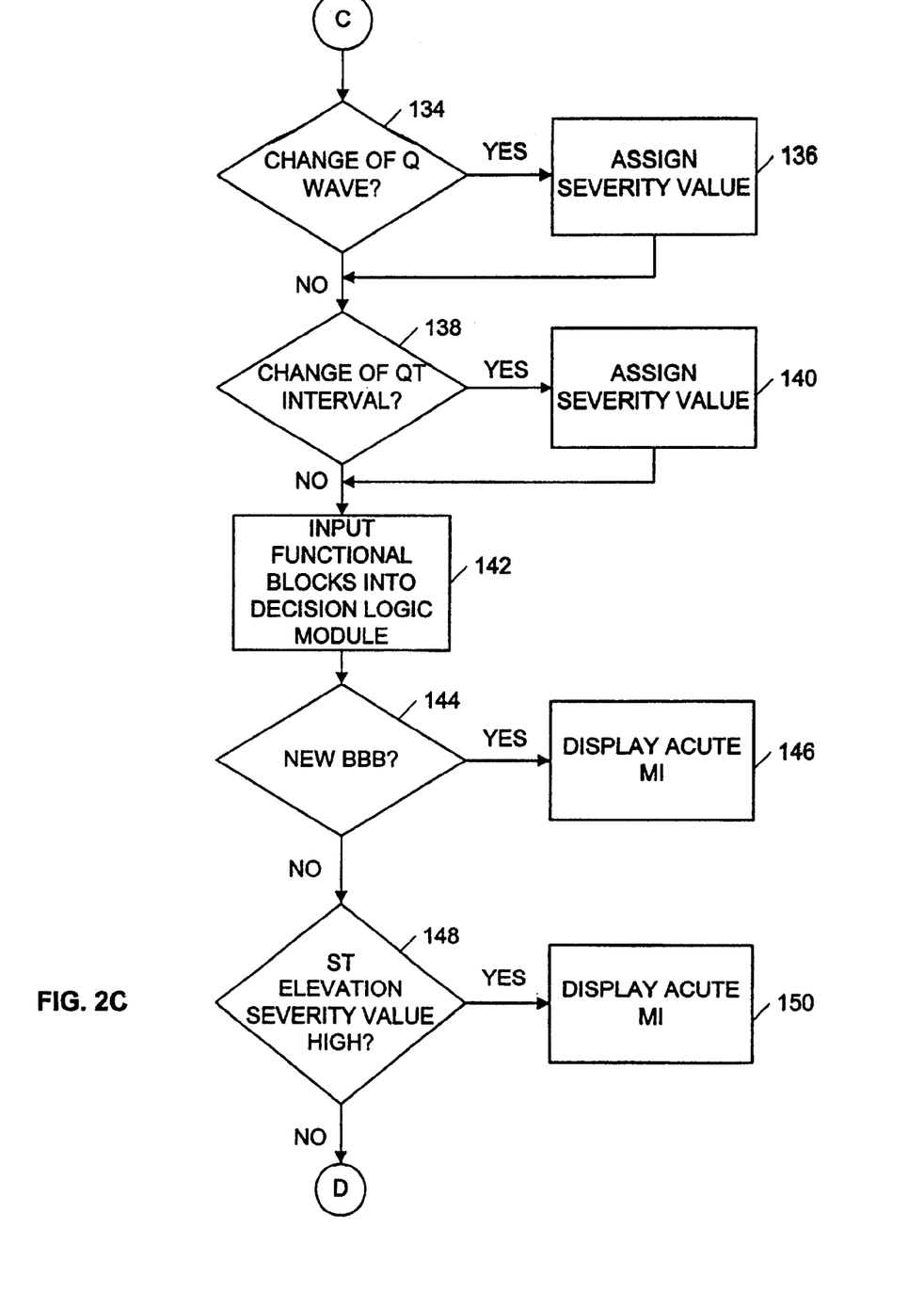
Figure 3:
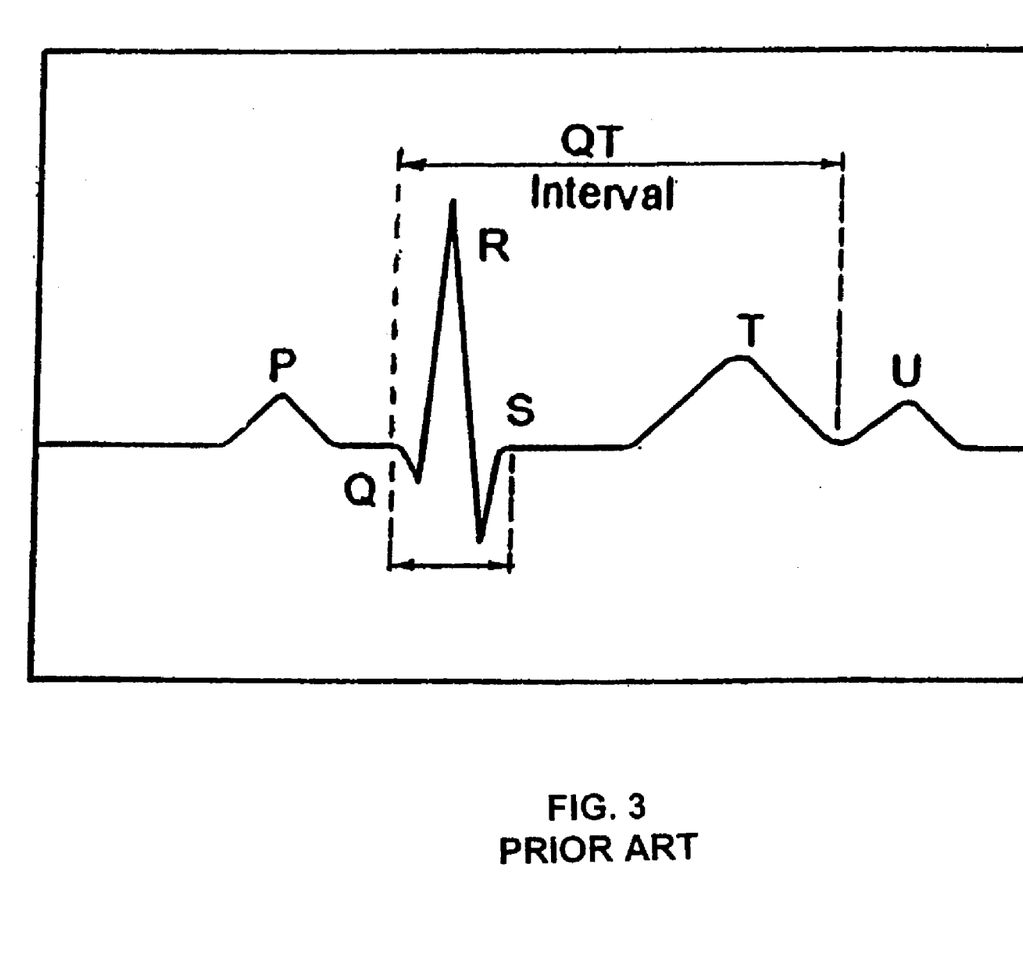
FIG. 3 illustrates a typical ECG waveform.

Referring to FIGS. 1 and 2C, the management module 26 then analyzes each of the sets of corresponding leads to determine (at 134) if there is a change in the Q wave in order to detect acute and non-acute myocardial infarction. The management module 26 determines if there are changes in the amplitude and duration of the Q wave. The sets of corresponding leads indicating a change in the Q wave are divided into the Q wave functional block. Once all the sets of corresponding leads are analyzed and divided, the management module 26 assigns (at 136) a severity value to the Q wave functional block. Preferably, if the duration of the Q wave of the first lead of the sets of corresponding leads is less than 40 milliseconds and the duration of the Q wave of the second lead of the sets of corresponding leads is greater than 40 milliseconds, a moderate severity level is assigned to the Q wave functional block. Similarly, if the duration of the Q wave of the first lead of the sets of corresponding leads is less than 40 milliseconds and the duration of the Q wave of the second lead of the sets of corresponding leads is greater than 60 milliseconds, a high severity level is assigned to the Q wave functional block.

Finally, the management module 26 analyzes each of the corresponding leads to determine (at 138) if there is a change in the QT interval in order to detect acute ischemia. The sets of corresponding leads indicating a change in the QT interval are divided in to the QT interval functional block. Once all the sets of corresponding leads are analyzed and divided, the management module 26 assigns (at 140) a severity value to the QT interval functional block. Preferably, the corrected QT interval (QTC) is analyzed by the management module 26. The QTC is the QT interval multiplied by the square root of the heart rate of the patient 14 divided by sixty [i.e., QTC=(QT interval)×sqrt (heart rate/60)]. If the QTC of the first lead of the sets of corresponding leads is less than 450 milliseconds and the QTC of the second lead of the sets of corresponding leads is greater than 450 milliseconds, a moderate severity value is assigned to the QT interval functional block. If the QTC of the first lead of the sets of corresponding leads is less than 450 milliseconds and the QTC of the second lead of the sets of corresponding leads is greater than 480 milliseconds, a high severity value is assigned to the QT interval functional block.

Although the analysis performed by the management module 26 is described above and shown in the drawings in a particular order, the analysis may be performed in any order and still be within the scope of the invention. Moreover, each and every step in the analysis described above and shown in the drawings does not have to be performed to be within the scope of the invention.

Once each of the sets of corresponding leads are divided into functional blocks and each of the functional blocks are assigned severity values, the functional blocks are input (at 142) into the decision logic module 28. The decision logic module 28 is used to implement a fuzzy logic algorithm. Fuzzy logic algorithms differ from conventional, fixed-value logic algorithms in that fuzzy logic algorithms use smoothed, membership functions to define the boundaries between groups. A set of fuzzy logic rules defines how the membership functions are combined. The fuzzy logic algorithm then makes decisions based on the output of the entire set of fuzzy logic rules.

According to the fuzzy logic algorithm, the decision logic module 28 first determines (at 144) whether the severity value assigned to the QRS functional block is high, indicating a new bundle branch block, i.e., either left bundle branch block or right bundle branch block. If the QRS functional block does indicate a new bundle branch block, the display 30 indicates (at 146) acute myocardial infarction to a clinician.

The decision logic module 28 then determines (at 148) whether the ST elevation functional block has been assigned a high severity value. If the ST elevation functional block has been assigned a high severity value, the display 30 indicates (at 150) acute myocardial infarction to a clinician.

Figure 2D:
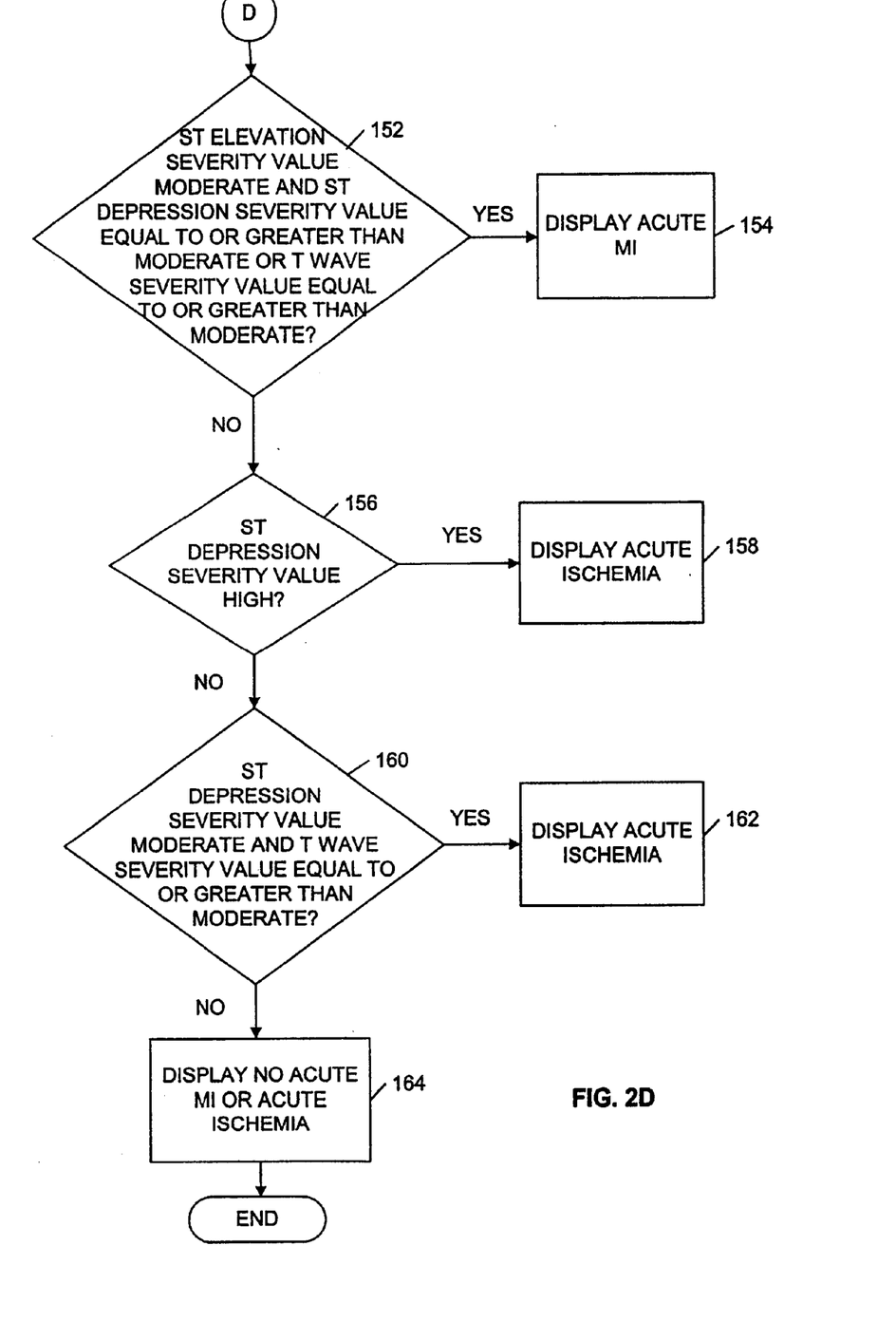

Referring to FIGS. 1 and 2D, the decision logic module 28 next determines (at 152) whether the ST elevation functional block has been assigned a moderate severity value. The decision logic module 28 also determines whether the ST depression functional block has been assigned a moderate severity value. The decision logic module 28 also determines whether the T wave functional block has been assigned a "moderate" severity value. If the decision logic module 28 determines (at 152) that the ST elevation functional block has been assigned a moderate severity value and, at the same time, the ST depression functional block has been assigned a severity value equal to or greater than moderate, the display 30 indicates (at 154) an acute myocardial infarction to a clinician. In addition, if the decision logic module 28 determines (at 152) that the T wave functional block has been assigned a severity value equal to or greater than moderate, the display 30 indicates (at 154) an acute myocardial infarction to a clinician.

The decision logic module 28 next determines (at 156) whether the ST depression functional block has been assigned a high severity value. If the decision logic module 28 determines (at 156) that the ST depression functional block has been assigned a high severity value, the display 30 indicates (at 158) acute ischemia to a clinician.

The decision logic module 28 next determines (at 160) whether the ST depression functional block has been assigned a moderate severity value. The decision logic module 28 also determines (at 160) whether the T wave functional block has been assigned a moderate severity value. If the decision logic module 28 determines (at 160) that the ST depression functional block has been assigned a moderate severity value and the T wave functional block has been assigned a severity value equal to or greater than moderate, the display 30 indicates (at 162) acute ischemia to a clinician. If the decision logic module 28 determines (at 160) that the ST depression functional block has not been assigned a moderate severity value, or the T wave functional block has not been assigned a moderate severity value, the display 30 indicates (at 164) to a clinician that the patient 14 is not suffering from either acute myocardial infarction or acute ischemia. If the patient 14 is not suffering from either acute myocardial infarction or acute ischemia, the clinician may determine and treat the cause of the patient's chest pain or the clinician may discharge the patient 14 from the emergency room.

Although the decisions of the fuzzy logic algorithm implemented by the decision logic module 28 are described above and shown in the drawings in a particular order, the decisions may be implemented in a fuzzy logic algorithm in any order and still be within the scope of the invention. Moreover, each and every decision described above and shown in the drawings does not have to be implemented in the fuzzy logic algorithm to be within the scope of the invention.

Various features and advantages of the invention are set forth in the following claims.

What is claimed is:

1. An acquisition device for acquiring electrocardiograms from a patient, the device comprising:
   an acquisition module for acquiring a plurality of electrocardiograms from the patient; and
   a signal processor coupled to the acquisition module for performing a serial comparison between at least two of the plurality of electrocardiograms,
   the plurality of electrocardiograms including an index electrocardiogram and at least one subsequent electrocardiogram, and
   the signal processor performing a serial comparison between the index electrocardiogram and the at least one subsequent electrocardiogram.

2. The device of claim 1 wherein the signal processor performs the serial comparison between the at least two of the plurality of electrocardiograms in real-time in order to detect an acute coronary syndrome.

3. The device of claim 1 wherein the plurality of electrocardiograms includes a baseline electrocardiogram, and wherein the signal processor performs a serial comparison between the baseline electrocardiogram and the index electrocardiogram and the at least one subsequent electrocardiogram.

4. The device of claim 3 wherein the baseline electrocardiogram is an electrocardiogram acquired from the patient during a stable cardiac period.

5. The device of claim 3 wherein an electrocardiogram management system is coupled to the acquisition device for accessing the baseline electrocardiogram.

6. The device of claim 5 and further comprising a receiver coupled to the acquisition device, and wherein the electrocardiogram management system is wirelessly coupled to the receiver in order to transmit the baseline electrocardiogram to the acquisition device.

7. The device of claim 6 and further comprising a transmitter coupled to the acquisition device, and wherein the electrocardiogram management system is wirelessly coupled to the transmitter in order to receive the index electrocardiogram and the at least one subsequent electrocardiogram from the acquisition device.

8. The device of claim 5 and further comprising memory coupled to the acquisition module for storing the baseline electrocardiogram in the acquisition device.

9. The device of claim 1 wherein the signal processor includes a management module and a decision logic module.

10. The device of claim 9 and further comprising a display coupled to the decision logic module, and wherein the display indicates to a clinician an output of the decision logic module.

11. The device of claim 9 wherein the management module compares the at least two of the plurality of electrocardiograms according to a plurality of functional blocks.

12. The device of claim 11 wherein the plurality of functional blocks includes at least one of P wave, Q wave, QRS complex, ST elevation, ST depression, T wave, and QT interval.

13. The device of claim 12 wherein the management module assigns a severity value for each one of the plurality of functional blocks based on a predetermined level of change.

14. The device of claim 13 wherein the decision logic module analyzes the severity value of each one of the plurality of functional blocks according to a fuzzy logic algorithm.

15. The device of claim 14 wherein the decision logic module outputs an indication of an acute myocardial infarction if the fuzzy logic algorithm determines that the QRS complex functional block has a high severity value and indicates a new bundle branch block.

16. The device of claim 14 wherein the decision logic module outputs an indication of an acute myocardial infarction if the fuzzy logic algorithm determines that the ST elevation functional block has a high severity value.

17. The device of claim 14 wherein the decision logic module outputs an indication of an acute myocardial infarction if the fuzzy logic algorithm determines that the ST elevation functional block has a moderate severity value and the ST depression functional block has a severity value equal to or greater than moderate or that the T wave functional block has a severity value equal to or greater than moderate.

18. The device of claim 14 wherein the decision logic module outputs an indication of acute ischemia if the fuzzy logic algorithm determines that the ST depression functional block has a moderate severity value and the T wave functional block has a severity value equal to or greater than moderate.

19. The device of claim 14 wherein the decision logic module outputs an indication of acute ischemia if the fuzzy logic algorithm determines that the ST depression functional block has a high severity value.

20. The device of claim 19 wherein the acquisition device is a one of a cardiograph, a Holter monitor, an event recorder, and a stress electrocardiogram machine.

21. A method of performing serial comparison between electrocardiograms acquired from a patient, the method comprising the acts of:
acquiring a plurality of electrocardiograms from the patient with an acquisition device, including acquiring an index electrocardiogram and at least one subsequent electrocardiogram; and
using the acquisition device to perform a serial comparison between at least two of the plurality of electrocardiograms, including performing a serial comparison between the index electrocardiogram and the at least one subsequent electrocardiogram.

22. The method of claim 21 wherein the act of using the acquisition device to perform a serial comparison between at least two of the plurality of electrocardiograms includes the act of comparing the at least two of the plurality of electrocardiograms in real-time in order to detect an acute coronary syndrome.

23. The method of claim 21 and further comprising the acts of accessing a baseline electrocardiogram and using the acquisition device to perform a serial comparison between the baseline electrocardiogram and the index electrocardiogram and the at least one subsequent electrocardiogram.

24. The method of claim 23 wherein the act of accessing a baseline electrocardiogram includes the act of accessing an electrocardiogram acquired from the patient during a stable cardiac period.

25. The method of claim 23 wherein the act of accessing a baseline electrocardiogram includes the act of accessing the baseline electrocardiogram from an electrocardiogram management system.

26. The method of claim 25 wherein the act of accessing the a baseline electrocardiogram from an electrocardiogram management system includes the act of wirelessly transmitting the baseline electrocardiogram from the electrocardiogram management system to the acquisition device.

27. The method of claim 26 and further comprising the act of wirelessly transmitting the index electrocardiogram and the at least one subsequent electrocardiogram from the acquisition device to the electrocardiogram management system.

28. The method of claim 27 and further comprising storing the at least one baseline electrocardiogram in the acquisition device.

29. The method of claim 21 wherein the act of using the acquisition device to perform a serial comparison between at least two of the plurality of electrocardiograms includes the act of performing a serial comparison according to a plurality of functional blocks, and wherein the plurality of functional blocks includes at least one of P wave, Q wave, QRS complex, ST elevation, ST depression, T wave, and QT interval.

30. The method of claim 29 and further comprising the act of assigning a severity value for each one of the plurality of functional blocks based on a predetermined level of change.

31. The method of claim 30 and further comprising the act of analyzing the severity value of each one of the plurality of functional blocks according to a fuzzy logic algorithm.

32. The method of claim 31 and further comprising the act of indicating an acute myocardial infarction to a clinician if the QRS complex functional block has a high severity value and indicates a new bundle branch block.

33. The method of claim 31 and further comprising the act of indicating to a clinician an acute myocardial infarction if the ST elevation functional block has a high severity value.

34. The method of claim 31 and further comprising the act of indicating to a clinician an acute myocardial infarction if the ST elevation functional block has a moderate severity value and the ST depression functional block has a severity value equal to or greater than moderate or if the T wave functional block has a severity value equal to or greater than moderate.

35. The method of claim 31 and further comprising the act of indicating to a clinician acute ischemia if the ST depression functional block has a high severity value.

36. The method of claim 31 and further comprising the act of indicating to a clinician acute ischemia if the ST depression functional block has a moderate severity value and the T wave functional block has a severity value equal to or greater than moderate.

37. A method of performing serial comparison between electrocardiograms acquired from a patient, the method comprising the acts of:
acquiring an index electrocardiogram and at least one subsequent electrocardiogram from the patient;
identifying changes between the index electrocardiogram and the at least one subsequent electrocardiogram in at least one of QRS complex, ST elevation, ST depression, and T wave;
assigning severity values to the identified changes, and analyzing the severity values according to a fuzzy logic algorithm;
indicating an acute myocardial infarction to a clinician if the severity value of the changes in the QRS complex is high, if the severity value of the changes in the ST elevation is high, if the severity value of the changes in the ST elevation and the ST depression are equal to or greater than moderate, or if the severity value of the changes in the T wave is equal to or greater than moderate; and
indicating acute ischemia to a clinician if the severity value of the changes in the ST depression is high or if the severity level of the changes in the ST depression and the T wave are equal to or greater than moderate.

38. The method of claim 37 wherein the act of identifying changes between the index electrocardiogram and the at least one subsequent electrocardiogram includes the act of identifying changes in real-time in order to detect an acute coronary syndrome.

39. The method of claim 37 wherein the act of assigning severity values to the changes includes the act of assigning a severity value based on a predetermined level of change.

40. The method of claim 37 and further comprising the acts of accessing a baseline electrocardiogram and identifying changes between the baseline electrocardiogram and the index electrocardiogram and the at least one subsequent electrocardiogram.

41. The method of claim 40 wherein the act of accessing a baseline electrocardiogram includes the act of accessing an electrocardiogram acquired from the patient during a stable cardiac period.

42. The method of claim 40 wherein the act of accessing a baseline electrocardiogram includes the act of accessing the baseline electrocardiogram from an electrocardiogram management system.

43. A software program for implementation in an electrocardiogram acquisition device and for performing a serial comparison between at least two electrocardiograms acquired from a patient, the software program comprising:

a management module for analyzing corresponding leads of the at least two electrocardiograms, for determining which corresponding leads indicate differences between the at least two electrocardiograms, for sorting the corresponding leads into a plurality of groups according to the indicated differences, and for assigning a severity value to each one of the plurality of groups; and a decision logic module for implementing a fuzzy logic algorithm to analyze the severity value assigned to each one of the plurality of groups and for outputting an indication of an acute coronary syndrome based on the analysis.

44. The software program of claim 43 wherein the electrocardiogram acquisition device is a one of a cardiograph, a Holter monitor, an event recorder, and a stress electrocardiogram machine.

45. The software program of claim 43 wherein the plurality of groups includes at least one of P wave, Q wave, QRS complex, ST elevation, ST depression, T wave, and QT interval.

46. The software program of claim 45 wherein the decision logic module outputs an indication of an acute myocardial infarction if the fuzzy logic algorithm determines that the QRS complex group has a high severity value and indicates a new bundle branch block.

47. The software program of claim 45 wherein the decision logic module outputs an indication of an acute myocardial infarction if the fuzzy logic algorithm determines that the ST elevation group has a high severity value.

48. The software program of claim 45 wherein the decision logic module outputs an indication of an acute myocardial infarction if the fuzzy logic algorithm determines that the ST elevation group has a moderate severity value and the ST depression group has a severity value equal to or greater than moderate or that the T wave group has a severity value equal to or greater than moderate.

49. The software program of claim 45 wherein the decision logic module outputs an indication of acute ischemia if the fuzzy logic algorithm determines that the ST depression group has a high severity value.

50. The software program of claim 45 wherein the decision logic module outputs an indication of acute ischemia if the fuzzy logic algorithm determines that the ST depression group has a moderate severity value and the T wave group has a severity value equal to or greater than moderate.

* * * * *